United States Patent [19]
Gillet et al.

[11] Patent Number: 5,780,673
[45] Date of Patent: Jul. 14, 1998

[54] PROCESS FOR THE PREPARATION OF ALKYL HALODIFLUOROACETATES

[75] Inventors: Jean-Philippe Gillet, Brignais; Christophe Ruppin, Pierre-Benite, both of France

[73] Assignee: Elf Atochem S.A., Puteaux, France

[21] Appl. No.: 864,782

[22] Filed: May 29, 1997

[30] Foreign Application Priority Data

May 29, 1996 [FR] France .................................. 96 06602

[51] Int. Cl.$^6$ ...................................................... C07C 69/63
[52] U.S. Cl. ............................................................. 560/227
[58] Field of Search .................................. 560/226, 227

[56] References Cited

U.S. PATENT DOCUMENTS 5.619,023  4/1997  Drivon et al. ...................... 204/157.6

*Primary Examiner*—Samuel Barts
*Attorney, Agent, or Firm*—Millen, White, Zelano & Branigan, P.C.

[57] ABSTRACT

A process for the preparation of alkyl halodifluoroacetates comprises reacting a 1,1-difluorotetrahaloethane with an alcohol, e.g., ethanol or isopropanol, in the presence of oxygen and a chemical free-radical initiator, e.g., an azo compound.

20 Claims, No Drawings

PROCESS FOR THE PREPARATION OF ALKYL HALODIFLUOROACETATES

FIELD OF THE INVENTION

The present invention relates to a process for the direct preparation of alkyl halodifluoroacetates by reaction 1,1-difluorotetrahaloethanes with an alcohol.

BACKGROUND OF THE INVENTION

Alkyl halodifluoroacetates are known intermediates in the synthesis of pharmaceutical and plant-protection products.

Many methods have been described for obtaining these alkyl halodifluoroacetates.

Usually, these methods use the reaction of an alcohol with a halodifluoroacetic acid, or preferably with the corresponding fluorides and chlorides.

These halodifluoroacetyl halides (fluoride or chloride) may be obtained according to very varied techniques.

U.S. Pat. No. 5,259,938 describes a process for the preparation of ω-halodifluoroacetyl chloride $M(CF_2)_nCOCl$, with M=F or Cl and n ranging from 1 to 10, by photochemical oxidation, in the presence of chlorine, of compounds of formula $M(CF_2)_nCH_xCl_y$ with x=1 or 2, given than x+y=3.

In the Journal of Organic Chemistry, 33 (2) pp. 816–9, (1968), a process is described for gaining access to bromodifluoroacetyl chloride, this process including the following steps:

$$CF_2=CF_2+NaOCH_3 \xrightarrow{THF}$$

$$CF_2=C(F)(OCH_3) \xrightarrow{bromine} \longrightarrow CF_2BrCFBrOCH_3$$

$$CF_2BrCFBrOCH_3 + 2ClSO_3H \longrightarrow CF_2BrC(O)Cl$$

The final yield of $CF_2BrC(O)Cl$ relative to the tetrafluoroethylene $C_2F_4$ is less than 30%.

Difluorohaloacetyl fluorides may also be obtained from $C_2F_4$.

In particular, bromodifluoroacetyl fluoride may be obtained according to the following steps described in the Japanese patent application published under the No. JP 82 40434:

$CF_2BrCF_2Br$ (obtained according to $CF_2=CF_2+Br_2)+S_{O3}$ (or $HSO_3F$) gives an intermediate containing the $BrCF_2CF_2OSO_2-$ group.

This intermediate is heated with $H_2SO_4$ or KF/sulpholane and leads to bromodifluoroacetyl fluoride $CF_2BrC(O)F$.

The methods most frequently cited consist, however, in carrying out a sulphuric hydrolysis, in the presence of mercuric salts, of 1,1-difluorotetrahaloethanes such as: $CF_2BrCFClBr$, $CF_2ClCCl_3$.

Thus, D. Morel & F. Dawans (Tetrahedron, 33 (12) pp. 1445–7) mention that 1,2-dibromochlorotrifluoroethane, obtained by bromination of chlorotrifluoroethylene, is hydrolysed in oleum medium in the presence of HgO according to the reaction:

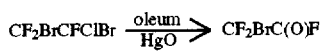

With 30–40% oleum, the amount of HgO used to activate the reaction is about 1% by weight relative to $CF_2BrCFClBr$.

If the oleum concentration is greater than 60%, the mercury oxide can be dispensed with.

Patent DE 1,020,970 describes the preparation of $CF_2ClC(O)Cl$ according to an analogous method, which consists in treating $CF_2ClCClBr_2$ with an oleum in the presence of $HgSO_4$ at a temperature in the region of 50° C., according to the reaction:

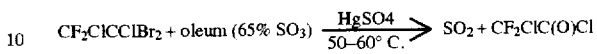

The $CF_2ClC(O)Cl$ may be purified by catalytic chlorination in the gas phase and then separated by fractional distillation.

It should also be noted that perhalo olefin oxides such as tetrafluoroethylene oxide or

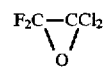

may be used as starting materials.

Patent EP 380,129 describes the preparation of $CF_2BrC(O)F$ according to the reaction:

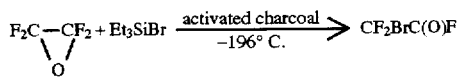

Lastly, it is pointed out that Chang-Ming Hu et al. (Journal of Fluorine Chemistry, 49 (1990) pp. 275–280) have described a fairly general method which converts a haloethane into the corresponding acid by reacting stoichiometric amounts of polyfluoroperhaloalkane and a redox pair consisting of ammonium persulphate and sodium formate.

Thus, 1,1-difluorotetrachloroethane is converted into chlorodifluoroacetic acid according to the reaction:

$CF_2ClCCl_3+(NH_4)_2$ $S_2O_8+HCO_2Na$, $2H_2O \rightarrow CF_2ClCOOH$ (66.5% yield - 100% conversion)

The reaction is carried out at 30° C. in DMF medium with air bubbled through. Once the reaction is complete, the medium is poured into water and the highly acidic solution is extracted with ether. The ether extract is neutralized with aqueous $NaHCO_3$ solution. The aqueous phase is evaporated to dryness and the residue ($CF_2ClCO_2Na$) is then taken up in concentrated $H_2SO_4$ and then distilled.

All these methods have many drawbacks. They usually use corrosive reaction media (oleum - concentrated $H_2SO_4$), environmentally hazardous catalysts (mercury salts) or else make use of reactions which are liable to evolve corrosive gases such as HF. This entails, on the one hand, specific and expensive items of apparatus (PVDF or PTFE cladding), and, on the other hand, complex treatments of the effluents if it is desired to protect the environment.

Moreover, it should be noted that certain starting materials are difficult to gain access to or are dangerous to handle, requiring very specific items of equipment.

SUMMARY OF THE INVENTION

The process which forms the subject of the present invention makes it possible to obtain directly, in a simple manner and in high yields, starting with readily accessible reagents, alkyl halodifluoroacetates of formula $$CF_2X-\underset{\underset{O}{\|}}{C}-OR \qquad (I)$$

in which X represents a fluorine, chlorine, bromine or iodine atom,

R represents a linear or branched aliphatic hydrocarbon radical having a carbon number ranging from 1 to 10, and preferably ranging from 1 to 8, this process being characterized in that it comprises:

1/ placing a 1,1-difluorotetrahaloethane of formula:

$$CF_2XCY_2Z \qquad (II)$$

in which X has the same meaning as in formula (I), Y and Z, which may be identical or different, represent a bromine, chlorine or iodine atoms, in contact with a sufficient amount of an alcohol ROH (III), R having the same meaning as in formula (I), preferably according to an $ROH/CF_2XCY_2Z$ molar ratio of not more than 30 and especially between 5 and 20, in the presence of oxygen and a sufficient minor molar amount p of at least one chemical free-radical initiator;

2/ heating the reaction medium obtained in step 1/ to a temperature at least equal to 40° C. and preferably between 60° C. and 80° C.;

3/ introducing continuously or by successive additions, while at the same time maintaining the temperature of step 2/, i.e., at least equal to 40° C., and preferably always in the presence of oxygen, a major molar amount q of at least one chemical free-radical initiator such that the molar ratio $p+q/CF_2XCY_2Z$ is between 0.01 and 0.2 and preferably between 0.05 and 0.1 to form that alkyl halodifluorinate (I);

In addition, it is preferred to recover the alkyl difluorinate by performing the following additional steps 4/ cooling the reaction medium to room temperature and then in extracting a crude product by distillation of the said reaction medium, then in subjecting the said crude product to distillation in the presence of an aliphatic, cycloaliphatic or aromatic solvent; and 5/ recovering the alkyl halodifluoroacetate (I).

According to the present invention, the term crude product is understood to refer to a mixture comprising water, excess ROH, the alkyl halodifluoroacetate (I), the unconverted 1,1-difluorotetrahaloethane (II) and various by-products. This crude product represents at least 60% and preferably 70% by weight of the reaction medium.

By way of illustration of 1,1-difluorotetrahaloethanes (II) which may be used according to the present invention, mention may be made of the compounds of formula:

$CF_2BrCCl_2Br, CF_2ClCCl_2I, CF_2BrCCl_2I, CF_3CBr_3$.

All of these compounds are obtained in a known manner and do not form the subject of the present invention.

It would not constitute a departure from the scope of the invention if step 1/ was carried out in the presence of water. This weight amount of water may vary within a wide range and may be up to 50% of the total mass of the reagents.

By way of illustration of alcohol ROH which may be used according to the present invention, mention may be made of methanol, ethanol, isopropanol, propanol, n-butanol or 2-ethylhexanol.

By way of illustration of chemical free-radical initiator which may be used according to the present invention, mention may be made of hydrogen peroxide, organic peroxides such as benzoyl peroxide, lauroyl peroxide, acetyl-cyclohexanesulphonyl peroxide, isobutyryl peroxide, dichloroacetyl peroxide, trichloroacetyl peroxide; organic hydroperoxides such as tert-butyl hydroperoxide, tert-amyl hydroperoxide, cumene hydroperoxide, para-menthane hydroperoxide; peroxydicarbonates such as ethyl peroxydicarbonate, ethylhexyl peroxydicarbonate, isopropyl peroxydicarbonate, isobutyl peroxydicarbonate, cetyl peroxydicarbonate, cyclohexyl peroxydicarbonate, myristyl peroxydicarbonate, tert-butylcyclohexyl peroxydicarbonate; tert-butyl perneodecanoate, cumyl perneodecanoate; tert-butyl permethoxyacetate; tert-butyl perethoxyacetate; azo compounds such as 2,2'-azobis(2,4-dimethylvaleronitrile), 1,1-azobis(cyclohexanecarbonitrile), azobis(isobutyronitrile), 2,2'-azobis(2-methylbutyronitrile).

Among these chemical initiators, it is preferred to use azo compounds such as azobis(isobutyronitrile) referred to as AIBN or 2,2'-azobis(2-methylbutyronitrile) referred to as AMBN. It is most particularly preferred to use AMBN.

According to the present invention, identical or different chemical free-radical initiators may be used in steps 1/ and 2/, but preferably an identical initiator will be used.

According to the present invention, the expression minor molar amount p of a chemical free-radical initiator is understood to refer to a molar amount which is not more than 40% and preferably between 10% and 20% pf the total molar amount p+q used in steps 1/ and 3/ of the process.

As solvent which can form an azeotrope with ROH and/or water, any non-alcoholic solvent which must not either be reactive towards the reagents (II) and (III) or have an influence on the products formed (I) may be used.

It must also be totally inert under the operating conditions of the distillation. By way of illustration of such solvents which can be used according to the present invention, mention may be made of linear paraffins such as hexane and heptane, cycloparaffins such as cyclohexane and cycloheptane, and aromatics such as toluene, benzene, cumene and xylenes.

According to the present invention, a weight amount of solvent of between 50% and 200%, and preferably an amount of between 60% and 100%, relative to the crude product will be used.

According to a variant of the process, it is possible to proceed by adding, in step 1/, a solvent which is identical or different to that used in step 4/. In this variant, the extraction operation is replaced by distillation of the crude product from the reaction medium.

According to the present invention, the duration of step 3/ may vary within a wide range. It is at least equal to 1 hour and preferably between 6 hours and 24 hours.

According to the present invention, the reaction is carried out in the presence of oxygen or air, or alternatively air enriched with oxygen, or alternatively again an inert gas such as nitrogen or argon enriched with oxygen. According to the present invention, the process will be performed with a molar amount of oxygen at least equal to 1 mol per mol of (II) used.

The process is generally performed at atmospheric pressure ($10^5$ Pa), but it would not constitute a departure from the scope of the invention if a different pressure was used.

The invention applies most particularly to the preparation of ethyl bromodifluoroacetate, ethyl chlorodifluoroacetate and ethyl trifluoroacetate.

In general, the products of formula (I) are prepared in any device which allows good dispersion of oxygen in the reaction medium.

The process will be performed most particularly in a vertical cylindrical (glass) reactor fitted with a jacket in which a heat-exchange fluid or a coolant may circulate, equipped with an ascending condenser linked with a hydraulic guard, a dip tube, a point for measuring the temperature and an introduction point, and the base of which consists of a porous plate via which oxygen is diffused into the reactor.

The porosity of the plate at the base of the said reactor is such that it allows good diffusion of oxygen into the reaction medium.

The said reactor may optionally be fitted with a stirrer or alternatively a recirculating loop.

The products of formula (I) are advantageously prepared according to the following procedure. The 1,1-difluorotetrahaloethane (II), the alcohol ROE (III), an amount p of chemical free-radical initiator and optionally water are introduced into a reactor as described above and under a stream of oxygen (the said oxygen arriving at the base of the said reactor and crossing the porous plate at the base of the reactor).

The reaction medium is heated while still under a stream of oxygen.

The amount q of chemical free-radical initiator is then introduced continuously or by successive additions.

Once the addition is complete, the reaction medium is cooled and a first distillation is then carried out, which allows a crude product as defined above to be extracted from the reaction medium. Next, this crude product is subjected to distillation in the presence of a solvent capable of forming one or more azeotropes (binary and/or ternary azeotropes) with the water and/or the alcohol. Next, the residue of this distillation is subjected to purification in order to recover the alkyl halodifluoroacetate (I). This purification usually consists in carrying out a distillation under reduced pressure.

The unconverted reagents, in particular such as the alcohol ROH and the solvent, may be recycled.

The products are analysed by gas chromatography and are identified by nuclear magnetic resonance.

The process which forms the subject of the present invention makes it possible to obtain alkyl halodifluoroacetates (I) directly, under mild operating conditions, by simple reaction between a 1,1-difluorotetrahaloethane and an alcohol, with a high conversion of the 1,1-difluorotetrahaloethane into ester. In addition, the effluents consist of products which may optionally be recycled, in particular such as the solvent.

The examples which follow illustrate the invention.

EXAMPLE 1

A stream of air at a flow rate of 8 l/h is introduced through a disperser into a 430 ml tubular reactor fitted with a jacket in which a heat-exchange fluid circulates, a gas disperser at its base (sintered glass), a gas inlet at the lower part of the said reactor, a condenser linked with a cooled trap, a dropping funnel, a temperature probe and a supply tube, after which the following are successively introduced:

74.03 g (i.e. 0.253 mol) of $CF_2BrCl_2Br$, 174.5 g (i.e. 3.789 mol) of ethanol, which corresponds to an ethanol/$CF_2BrCCl_2Br$ molar ratio equal to about 15, and 486 mg of 2,2'-azobis(2-methylbutyronitrile), referred to hereinafter as AMBN, as chemical free-radical initiator.

The mixture is heated to 70° C. by means of an oil circulating in the jacket.

The air flow rate of 8 l/h and the temperature of 70° C. are maintained for 12 hours, during which time 486 mg of AMBN are added every 2 hours, i.e. 5×486=2.430 g of AMBN (0.0126 mol). This corresponds to an initiator/$CF_2BrCCl_2Br$ molar ratio equal to:

$$\frac{0.0025. + 0.0126}{0.253} = 0.0596$$

The progress of the reaction is monitored by determining the conversion of $CF_2BrCCl_2Br$ by gas chromatographic analysis (GC) of samples taken from the reaction medium. The results are reported below:

| Reaction time (hours) | Conversion of $CF_2BrCCl_2Br$ (%) |
|---|---|
| 1 | 24 |
| 5 | 65 |
| 12 | 91 |

The reaction medium is cooled to room temperature. 236.4 g of a mixture are obtained, which mixture is subjected to distillation in an "Oldershaw" type 20-plate adiabatic column fitted with a timer.

The temperature at the foot of the column is brought to 88° C., the column is left to equilibrate and a crude product is removed from the head of the column with a 9/1 reflux, up to a temperature of 77.5° C. After 8 h 50 min of distillation, the distillation is stopped.

165.5 g of a crude product are obtained (about 70% by weight of the reaction mixture subjected to the distillation), which comprises ethanol (40% by weight), ethyl bromodifluoroacetate (19.57% by weight), water, etc.

This crude product is subjected to a second distillation in the presence of 100 g of cyclohexane in order to remove the water and the ethanol.

The same column as above is used.

The head of the column is fitted with a timer and a Florentine flask in order to recycle the organic phase (cyclohexane).

The temperature at the foot of the column is brought to 90° C., and the column is left to equilibrate. The water/ethanol/cyclohexane ternary azeotrope is distilled off at the head of the column, at a temperature of 62.1° C., after which the ethanol/cyclohexane binary azeotrope is distilled off at 64.9° C. with a 9/1 reflux.

The excess cyclohexane is then distilled off.

The ethyl bromodifluoroacetate (EBDFA) obtained at the foot of the column, in a purity of about 95%, is subjected to a further distillation under reduced pressure.

34 g of ethyl bromodifluoroacetate distilling at 57° C./58° C. at a pressure of 133.32 Pa (100 mm Hg) are obtained.

The purity determined by GC is 98.5%.

The molar yield of ethyl bromodifluoroacetate obtained (purity: 98.5%) is 68% relative to the $CF_2BrCCl_2Br$ used.

The ethyl bromodifluoroacetate was identified by proton ($^1H$), carbon 13 ($^{13}C$) and fluorine 19 ($^{19}F$) X nuclear magnetic resonance (NMR) on a Brucker AC300 multinuclear type machine (frequencies for $^1H$=300.13 MHz, for $^{13}C$=75.47 MHz and for $^{19}F$ 282.4 MHz).

NMR identification of

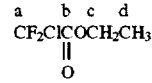

♦ $^{13}C$ NMR spectrum (solvent=$CDCl_3$)

δa=108.8 ppm

δb=159.5 ppm

δc=64.5 ppm

δd=13.5 ppm

♦ $^{19}F$ NMR spectrum (solvent=$CDCl_3$/external standard: trifluoroacetic acid)

$\delta(CF_2Br)=-16.8$ ppm coupling constant $J_{C-F}=314$ Hz coupling constant $J_{C-F}=31$ Hz ♦ $^1H$ NMR spectrum (solvent =$CDCl_3$/internal standard: tetramethylsilane)

$\delta(CH_2)=4.42$ ppm $\delta(CH_3)=1.40$ ppm

EXAMPLE 2

The process is performed in the same apparatus as in Example 1.

A stream of air is injected at a flow rate of 8 l/h through the disperser, after which the following are successively introduced:

38 g (i.e. 0.130 mol) of $CF_2BrCCl_2Br$, 87.2 g (i.e. 1.893 mol) of ethanol, which corresponds to an ethanol/$CF_2BrCCl_2Br$ molar ratio equal to 14.56, and 242.5 mg (i.e. 0.0013 mol) of AMBN.

The mixture is heated to 70° C. by means of an oil circulating in the jacket.

The air flow rate of 8 l/h and the temperature of 70° C. are maintained for 12 hours, during which time 15.15 g of an ethanolic stock solution of AMBN are injected continuously at a rate of 1.262 g/h.

This solution consists of 1.248 g (i.e. 0.0065 mol) of AMBN, 9.7 g of ethanol and 4.2 g (i.e. 0.143 mol) of $CF_2BrCCL_2Br$.

This corresponds to an initiator/$CF_2BrCCl_2Br$ molar ratio equal to:

$$\frac{0.0013 + 0.0065}{0.130 + 0.014} = 0.0542$$

As in Example 1, the reaction progress is monitored by determining the conversion of $CF_2BrCCl_2Br$ by GC analysis of samples taken from the reaction medium.

The results are reported below:

| Reaction time (hours) | Conversion of $CF_2BrCCl_2Br$ (%) |
| --- | --- |
| 1 | 18 |
| 5 | 45 |
| 12 | 72 |

The reaction medium is cooled to room temperature.

131.5 g of a mixture are obtained, which mixture is treated according to the distillation conditions of Example 1.

The crude product obtained after the first distillation (93 g) is subjected to a second distillation in the presence of 60 g of cyclohexane.

The ethyl bromodifluoroacetate obtained after distillation under reduced pressure has a purity identical to that obtained in Example 1.

14.25 g of ethyl bromodifluoroacetate are obtained, which corresponds to a molar yield of 54% relative to the total $CF_2BrCCl_2Br$ used.

EXAMPLE 3

The process is performed in the same apparatus as in Example 1 and according to identical operating conditions, except that 95% ethanol is used.

• Amount of reagents used:

37.12 g (i.e. 0.127 mol) of $CF_2BrCCl_2Br$, 93.21 g of 95% alcohol, which corresponds to 88.55 g of 100% ethanol, i.e. 1.922 mol and 4.66 g of water.

242.5 mg (i.e. 0.0013 mol) of AMBN.

The air flow rate is 8 l/h, the temperature is 70° C. and the reaction time is 12 hours, during which time 242.5 mg of AMBN are added every 2 hours.

This corresponds to an initiator/$CF_2BrCCl_2Br$ molar ratio equal to:

$$\frac{0.0013 + 5 \times 0.0013}{0.127} = 0.0614$$

The reaction progress is monitored by determining the conversion of $CF_2BrCCl_2Br$ as in the above examples.

The results are reported below:

| Reaction time (hours) | Conversion of $CF_2BrCCl_2Br$ (%) |
| --- | --- |
| 1 | 35 |
| 3 | 48 |
| 5 | 65 |
| 7 | 79 |
| 9 | 87 |
| 12 | 99 |

The reaction medium is cooled to room temperature.

119 g of a mixture are obtained, which mixture is treated according to the distillation conditions of Example 1.

The crude product obtained after the first distillation (about 85 g) is subjected to a second distillation in the presence of 70 g of cyclohexane.

After distillation under reduced pressure, 15.2 g of ethyl bromodifluoroacetate are obtained in a purity equal to about 98%, which corresponds to a molar yield of 59% relative to the $CF_2BrCCl_2Br$ used.

EXAMPLE 4

The process is performed in the same apparatus as in Example 1. A stream of air at a flow rate of 8 l/h is injected through the disperser and the following are then successively introduced:

37.21 g (i.e. 0.127 mol) of $CF_2BrCCl_2Br$, 114.08 g (i.e. 1.90 mol) of isopropanol, which corresponds to an isopropanol/$CF_2BrCCl_2Br$ molar ratio of 14.96; and 244.6 mg (i.e. 0.00127 mol) of AMBN.

The mixture is heated to 70° C. by means of an oil circulating in the jacket.

The air flow rate of 8 l/h and the temperature of 70° C. are maintained for 7 hours, during which time 242.6 mg of AMBN are added every two hours, i.e. 3×242.6=727.8 mg of AMBN (0.00379 mol). This corresponds to an initiator/ $CF_2BrCCl_2Br$ molar ratio equal to:

$$\frac{0.00127 + 0.00379}{0.127} \: 0.0398$$

As in Example 1, the reaction progress is monitored by determining the conversion of $CF_2BrCCl_2Br$ by GC analysis of samples taken from the reaction medium.

The results are reported below:

| Reaction time (hours) | Conversion of CF$_2$BrCCl$_2$Br (%) |
|---|---|
| 1 | 48 |
| 3 | 70 |
| 5 | 90 |
| 7 | 98 |

The reaction medium is cooled to room temperature.

142.3 g of a mixture are obtained, which mixture is treated according to the distillation conditions of Example 1. The crude product obtained after the first distillation (99.6 g) is subjected to a second distillation in the presence of 70 g of toluene.

The isopropyl bromodifluoroacetate obtained after distillation under reduced pressure has a purity of greater than 99%.

19.7 g of isopropyl bromodifluoroacetate are obtained, which corresponds to a molar yield of 71% relative to the CF$_2$BrCCl$_2$Br used.

EXAMPLE 5

The process is performed in the same apparatus as in Example 1. A stream of air is injected at a flow rate of 16 l/h through the disperser, after which the following are successively introduced:

- 35.31 g (i.e. 0.12 mol) of CF$_2$BrCCl$_2$I,
- 82.84 g (i.e. 1.8 mol) of ethanol, which corresponds to an ethanol/CF$_2$BrCCl$_2$I molar ratio of 15; and
- 0.1157 mg (i.e. 0.0006 mol) of AMBN.

The mixture is heated to 71° C.

The air flow rate of 16 l/h and the temperature of 71° C. are maintained for 2 hours, during which time 0.1157 g of AMBN are added every 30 minutes, i.e. 3×0.1157=0.3471 g of AMBN (0.0018 mol). This corresponds to an initiator/CF$_2$BrCCl$_2$I molar ratio equal to:

$$\frac{0.0006 + 0.0018}{0.1195} = 0.020$$

The conversion of CF$_2$BrCCl$_2$I after 2 hours is 81%.

The reaction medium is cooled to room temperature.

117.1 g of a mixture are obtained, which mixture is treated according to the distillation conditions of Example 1.

The crude product obtained after the first distillation (82 g) is subjected to a second distillation in the presence of 60 g of cyclohexane.

The ethyl chlorodifluoroacetate obtained after distillation under reduced pressure has a purity of about 99% (determined by GC).

The molar yield of ethyl chlorodifluoroacetate obtained (purity: 99%) is 65% relative to the CF$_2$BrCCl$_2$I used.

The ethyl chlorodifluoroacetate was identified by $^{13}$C, $^{19}$F and $^1$H NMR.

NMR identification of

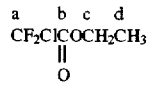

a b c d
CF$_2$ClCOCH$_2$CH$_3$
‖
O

- $^{13}$C NMR spectrum (solvent=CDCl$_3$)

δa=116.9 ppm
δb=159.2 ppm
δc=64.5 ppm
δd=13.7 ppm

- $^{19}$F NMR spectrum (solvent=CDCl$_3$/external standard TFA)

δ(C$\underline{F}_2$Cl)=−15.4 ppm $J^1{}_{C-F}$=300 Hz  $J^2{}_{C-F}$=34.5 Hz

- $^1$H NMR spectrum (solvent=CDCl$_3$/internal standard TMS)

δ(C$\underline{H}_2$)=4.4 ppm
δ(C$\underline{H}_3$)=1.4 ppm

The preceding examples can be repeated with similar success by substituting the generically or specifically described reactants and/or operating conditions of this invention for those used in the preceding examples.

The entire disclosure of all applications, patents and publications, cited above, and of corresponding French application No. 96/06602, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for the preparation of an alkyl halodifluoroacetate of formula:

CF$_2$X—C—OR  (I)
‖
O in which X represents a fluorine, chlorine, bromine or iodine atom, R represents a linear or branched aliphatic hydrocarbon radical having a carbon number ranging from 1 to 10, said process comprising:

1/ placing a 1,1-difluorotetrahaloethane of formula:

CF$_2$XCY$_2$Z  (II)

in which X has the same meaning as in formula (I), Y and Z, which may be identical or different, represent a bromine, chlorine or iodine atom, in contact with an alcohol ROR (III), R having the same meaning as in formula (I), in the presence of oxygen and a sufficient molar amount p of at least one chemical free-radical initiator;

2/ heating the reaction medium obtained in step 1/ to a temperature at least equal to 40° C.;

3/ introducing continuously or by successive additions, while at the same time maintaining a temperature of at least 40° C. and in the presence of oxygen and a molar amount q greater than molar amount p, of at least one chemical free-radical initiator such that the overall molar ratio p+q/CF$_2$XCY$_2$Z of the reaction is between 0.01 and 0.2 so as to form the alkyl halodifluoroacetate.

2. A process according to claim 1 comprising the further steps of:

4/ cooling the reaction medium to room temperature and then in extracting a crude product by distillation of the said reaction medium, then in subjecting the said crude product to distillation in the presence of an aliphatic, cycloaliphatic or aromatic solvent; and 5/ recovering the alkyl halodifluoroacetate (I).

3. A process according to claim 1, wherein the 1,1-difluorotetrahaloethane of formula (II) is CF$_2$BrCCl$_2$Br or CF$_2$BrCCl$_2$I.

4. A process according to claim 1, wherein the alcohol ROH (III) is ethanol or isopropanol.

5. A process according to claim 1, wherein the chemical free-radical initiator is an azo compound.

6. A process according to claim 5, wherein the azo compound is 2,2'-azobis(2-methylbutyronitrile).

7. A process according to claim 1, the minor molar amount p of chemical free-radical initiator is not more than 40% of the total molar amount p+q used.

8. A process according to claim 2, wherein the solvent is cyclohexane or toluene.

9. A process according to claim 1, carried out in the presence of air.

10. A process according to claim 1, carried out in the presence of water.

11. A process according to claim 3, wherein the alcohol ROH (III) is ethanol or isopropanol.

12. A process according to claim 11, wherein the chemical free-radical initiator is an azo compound.

13. A process according to claim 12, wherein the azo compound is 2,2'-azobis(2-methylbutyronitrile).

14. A process according to claim 13, wherein in step (1) the $ROH/CF_2XCY_2Z$ molar ratio is not more than 30.

15. A process according to claim 1, wherein in step 2, the heating is conducted to a temperature of between 60° and 80° C.

16. A process according to claim 1, wherein the overall molar ratio of $p+q/CF_2XCY_2Z$ is between 0.05 and 0.1.

17. A process according to claim 1, wherein the temperature in step (3) is the same as in step (2).

18. A process according to claim 1, wherein step (3) is conducted throughout in the presence of oxygen.

19. A process according to claim 1, wherein in step (1) the $ROH/CF_2XCY_2Z$ molar ratio is not more than 30.

20. A process according to claim 19, wherein the molar ratio is 5:1 to 20:1.

* * * * *